(12) United States Patent
Simons et al.

(10) Patent No.: US 9,700,211 B2
(45) Date of Patent: Jul. 11, 2017

(54) DENTAL APPARATUS AND METHOD OF UTILIZING THE SAME

(71) Applicant: KONINKLIJKE PHILIPS N.V., Eindhoven (NL)

(72) Inventors: Paul Richard Simons, Cambridge (GB); Steven Charles Deane, Cambridge (GB)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 14/442,830

(22) PCT Filed: Dec. 13, 2013

(86) PCT No.: PCT/IB2013/060896
§ 371 (c)(1),
(2) Date: May 14, 2015

(87) PCT Pub. No.: WO2014/097082
PCT Pub. Date: Jun. 26, 2014

(65) Prior Publication Data
US 2015/0297085 A1    Oct. 22, 2015

Related U.S. Application Data

(60) Provisional application No. 61/739,525, filed on Dec. 19, 2012.

(51) Int. Cl.
*A61C 19/00* (2006.01)
*A61B 5/00* (2006.01)
(Continued)

(52) U.S. Cl.
CPC .......... *A61B 5/0071* (2013.01); *A61B 5/0088* (2013.01); *A61B 5/4547* (2013.01);
(Continued)

(58) Field of Classification Search
CPC .... A61N 5/0601; A61N 5/062; A61N 5/6024; A61N 2005/0606; A61N 2005/0628;
(Continued)

(56) References Cited

U.S. PATENT DOCUMENTS 4,290,433 A    9/1981    Alfano
6,024,562 A    2/2000    Hibst et al.
(Continued)

FOREIGN PATENT DOCUMENTS

WO    9959462 A1    11/1999
WO    2011077282 A2    6/2011
(Continued)

*Primary Examiner* — Michael Carey

(57) ABSTRACT

A dental apparatus is provided. The dental apparatus includes a handle including a power button configured to place the dental apparatus in on/off configurations. A controller is housed within the handle and includes a mouth detection module and a tooth anomaly module. Electrical circuitry is in operable communication with the mouth detection module and tooth anomaly module and is configured to emit a low intensity excitation light having a first frequency and a high intensity excitation light which may have a second frequency. The low intensity excitation light is utilized to detect the presence of tooth material and the high intensity excitation light is utilized to detect the presence of a tooth anomaly or to treat a dental condition.

15 Claims, 2 Drawing Sheets

(51) Int. Cl.
*A61C 19/04* (2006.01)
*A61N 5/06* (2006.01)

(52) U.S. Cl.
CPC ........... *A61C 19/04* (2013.01); *A61N 5/0601* (2013.01); *A61B 2560/0209* (2013.01); *A61B 2560/0266* (2013.01); *A61N 2005/0606* (2013.01); *A61N 2005/0626* (2013.01); *A61N 2005/0644* (2013.01); *A61N 2005/0651* (2013.01); *A61N 2005/0667* (2013.01)

(58) Field of Classification Search
CPC .......... A61N 2005/0644; A61N 5/0624; A61B 5/0088; A61B 5/0071; A61B 5/4547; A61B 5/0601; A61C 19/06; A61C 19/04
USPC ............. 607/88, 90, 92, 93, 134, 94; 433/29
See application file for complete search history.

(56) References Cited

U.S. PATENT DOCUMENTS

| | | | |
|---|---|---|---|
| 6,186,780 B1 | 2/2001 | Hibst et al. | |
| 2008/0060148 A1* | 3/2008 | Pinyayev | A61B 5/0088 15/22.1 |
| 2010/0040993 A1* | 2/2010 | Karazivan | A61B 1/00105 433/29 |

FOREIGN PATENT DOCUMENTS

| | | | |
|---|---|---|---|
| WO | 2011077290 A1 | 6/2011 | |
| WO | 2014097022 A1 | 6/2014 | |

* cited by examiner

DENTAL APPARATUS AND METHOD OF UTILIZING THE SAME

CROSS-REFERENCE TO PRIOR APPLICATIONS

This application is the U.S. National Phase application under 35 U.S.C. §371 of International Application No. PCT/IB2013/060896, filed on Dec. 13, 2013, which claims the benefit of U.S. Provisional Patent Application No. 61/739,525, filed on Dec. 19, 2012. These applications are hereby incorporated by reference herein.

BACKGROUND

Technical Field

The present disclosure relates to a dental apparatus and method of utilizing the same. More particularly, the present disclosure relates to a dental apparatus and method of use of the dental apparatus utilizing a low intensity excitation light having a first frequency or intensity to detect when the dental apparatus is placed in a mouth of a user and a high intensity excitation light which may have a second frequency to detect dental plaque, or treat a dental condition.

Description of Related Art

Caries or periodontal diseases are thought to be infectious diseases caused by bacteria present in dental plaques. Removal of dental plaques is highly important for the health of oral cavities. Dental plaques, however, are not easy to identify by the naked eye. A variety of plaque detection apparatuses have been produced to aid in the detection of dental plaque and/or caries.

Most of the dental plaque detection apparatuses are configured for use by trained professionals and make use of the fact that the visible luminescence spectra from dental plaque (and/or caries) and non-decayed regions of a tooth are substantially different. Some dental plaque detection apparatuses are configured for use by consumers (whom are, typically, not trained dental professionals) in their own homes in helping consumers achieve good oral hygiene.

For example, one known type of dental plaque apparatus utilizes irradiated light to illuminate tooth material and gums to identify areas infected by biofilms and areas of dental plaque. This type of plaque detection apparatus may utilize a monochromatic excitation light and may be configured to detect fluorescent light in 2 bands 440-470 nm (e.g., blue light) and 560-640 nm (e.g., red light); the intensities are subtracted to reveal the dental plaque and/or caries regions.

While the aforementioned dental plaque apparatus are suitable for their intended use, they exhibit one or more shortcomings. Specifically, it is known that each area of the eye absorbs different wavelengths of light and, if too much light is absorbed by the eye, the eye may be damaged; this damage can occur even with extremely short exposure, although longer exposures create a greater the risk of eye tissue damage. The thresholds of the damages that can ensue from light energy may depend on one or more characteristics associated with the light, e.g., wavelength, spot size and pulse length of the light. Careful consideration of these properties of light need to be taken into consideration to assess the safety of the light being utilized to detect dental plaque and/or caries.

With respect to the wavelength of light, for example, the hazard potential of a near-infrared light could be considered from two perspectives: eye hazards and skin hazards. Specifically, since the eye produces focused light on the retina, the effect of focused light that may be generated by dental plaque apparatus during operation thereof may be greater than non-focused light, thus increasing the risk of injury. Further, because infrared light (e.g., red light) is not registered by the eye, the pupil of the eye would not close to protect the retina from focused light that may be generated by dental plaque apparatus during operation thereof; this is the same affect as with ultraviolet light, which causes "snow blindness." In addition, eyelids are, typically, thin and not able to protect the eye from the penetration of ultraviolet light (e.g., blue light); excessive ultraviolet exposure damages the cornea and the retina.

As can be appreciated, to avoid possible eye injury, it is imperative that a user not switch on the plaque detection apparatus until the plaque detection apparatus is appropriately placed inside the mouth. The aforementioned devices, however, are not configured to automatically detect when the plaque detection apparatus are placed inside the mouth. As a result thereof, potentially harmful radiation that could damage the eyes, or cause uncomfortable glare if exposed to the eyes, may result if proper handling precautions are not followed, e.g., consumer misuse.

SUMMARY

As can be appreciated, a dental apparatus and method of use of the dental apparatus utilizing a low intensity excitation light having a first frequency to detect when the dental apparatus is placed in a mouth of a user and a high intensity excitation light which may have a second frequency to detect dental plaque, or for other dental applications such as gingivitis treatment, halitosis reduction, or tooth whitening, may prove useful in dentistry.

An aspect of the instant disclosure provides a dental apparatus. The dental apparatus includes a handle including a power button configured to place the dental apparatus in on/off configurations. A controller is housed within the handle and includes a mouth detection module and a tooth anomaly module. Electrical circuitry is in operable communication with the mouth detection module and tooth anomaly module and is configured to emit a low intensity excitation light having a first frequency and a high intensity excitation light which may have a second frequency. The low intensity excitation light is utilized to detect the presence of tooth material and the high intensity excitation light is utilized to detect the presence of a tooth anomaly, or to treat a dental condition. The tooth anomaly may be biofilms, dental plaque and caries. The dental condition to be treated may be gingivitis, halitosis, or tooth staining.

A battery may be housed within the handle and configured to supply power to the dental apparatus including a motor that is housed within the handle and the electrical circuitry, which is housed in a shaft that extends distally from handle. A toothbrush assembly may be configured to releasably couple to the shaft for brushing teeth and removing the tooth anomaly. A window may be positioned on the toothbrush assembly adjacent a plurality of bristles provided thereon and aligns with the electrical circuitry disposed on the shaft such the high and low intensity excitation light is emitted through the window and into a mouth of a user.

The high intensity excitation light may be 5 times greater than the low intensity excitation light and the first frequency may be substantially equal to the second frequency. The electrical circuitry may include one or more light emitting diodes, filters, photodetectors and imaging sensors.

The dental apparatus may be operable in two modes of operation, a mouth detection mode that is configured to detect the presence of the tooth material and a dental plaque detection mode that is configured to detect the presence of the tooth anomaly. The controller may be configured to automatically switch between the mouth detection mode and dental plaque detection mode. Moreover, the controller may be configured to automatically default to the mouth detection mode when the dental apparatus is initially powered and when the dental apparatus is removed from a mouth of a user. Autofluorescence associated with the tooth material and the tooth anomaly may be detectable by the electrical circuitry and communicated to the controller for placing the dental apparatus in the mouth detection mode and dental plaque detection mode, respectively. In the dental plaque detection mode, the controller may be configured to continuously detect autofluorescence associated with the tooth material while continuously detecting autofluorescence associated with the tooth anomaly.

An aspect of the instant disclosure provides a dental apparatus. The dental apparatus includes a handle including a power button that is configured to place the dental apparatus in on/off configurations. A shaft extends distally from the handle. The handle houses a battery, a motor and a controller therein. The controller includes a mouth detection module and a tooth anomaly module. A toothbrush assembly is configured to removably couple to the shaft. Electrical circuitry is housed within the shaft and is in operable communication with the mouth detection module and tooth anomaly module. The electrical circuitry is configured to emit a low intensity excitation light having a first frequency and a high intensity excitation light having second frequency. The dental apparatus is operable in a mouth detection mode for detecting autofluorescence associated with tooth material such that detection of autofluorescence associated the tooth material places the dental apparatus in a dental plaque detection mode for detecting autofluorescence of a tooth anomaly. The tooth anomaly may be biofilms, dental plaque and caries.

A window may be positioned on the toothbrush assembly adjacent a plurality of bristles provided thereon and aligns with the electrical circuitry disposed on the shaft such the high and low intensity excitation light is emitted through the window and into a mouth of a user.

The high intensity excitation light may be 5 times greater than the low intensity excitation light and the first frequency may be substantially equal to the second frequency. The electrical circuitry may include one or more light emitting diodes, filters, photodetectors and imaging sensors.

The controller may be configured to automatically switch between the mouth detection mode and dental plaque detection mode. Moreover, the controller may be configured to automatically default to the mouth detection mode when the dental apparatus is initially powered and when the dental apparatus is removed from a mouth of a user. Autofluorescence associated with the tooth material and the tooth anomaly may be detectable by the electrical circuitry and communicated to the controller for placing the dental apparatus in the mouth detection mode and dental plaque detection mode, respectively. In the dental plaque detection mode, the controller may be configured to continuously detect autofluorescence associated with the tooth material while continuously detecting autofluorescence associated with the tooth anomaly.

An aspect of the instant disclosure provides a method for detecting dental plaque. A dental apparatus is, initially, positioned inside a mouth of a patient. A low intensity excitation light having a first frequency is, initially, emitted. Thereafter, autofluorescence of tooth material within the mouth is detected. Then, a high intensity excitation light having a second frequency is emitted. And, autofluorescence of a tooth anomaly is detected. The tooth anomaly may be biofilms, dental plaque and caries.

The high intensity excitation light utilized may be at least 5 times greater than the low intensity excitation light and the first frequency is substantially equal to the second frequency.

Emitting and detecting may be achieved via a dental apparatus that is positioned inside a mouth of a patient. The dental apparatus may be provided with a controller configured to automatically switch between a mouth detection mode and a dental plaque detection mode. The controller may be configured to automatically default to the mouth detection mode when the dental apparatus is initially powered and when the dental apparatus is removed from a mouth of a user.

A window that is positioned on a toothbrush assembly adjacent to a plurality of bristles provided thereon may be provided. The window may be aligned with electrical circuitry disposed on a shaft of the dental apparatus such that the high and low intensity excitation light is emitted through the window and into a mouth of a user. The electrical circuitry may be provided with one or more light emitting diodes, filters, photodetectors and/or an imaging sensors.

BRIEF DESCRIPTION OF THE DRAWINGS

The aspects of the present disclosure may be better understood with reference to the following figures. The components in the figures are not necessarily to scale, emphasis instead being placed upon clearly illustrating the principles of the disclosure. Moreover, in the figures, like reference numerals designate corresponding parts throughout the several views.

In the figures.

DETAILED DESCRIPTION

The present disclosure describes various embodiments of apparatuses and methods that utilize one or more power levels of excitation light for detecting one or more tooth anomalies such that the tooth anomalies may be removed. Specifically, a dental apparatus, e.g. an electric toothbrush, is configured to provide multiple power levels and/or frequencies of excitation light. More specifically, a first power level (e.g., less than 1 mW) of excitation light having a first frequency, e.g. blue light, is, initially, emitted from the dental apparatus and utilized to detect a distinct autofluorescence associated with tooth material to determine if the dental apparatus is positioned in a mouth. Thereafter, a second power level (e.g., less than 1 mW but greater than the first power lever) of excitation light having substantially the same frequency as the first frequency of excitation light is emitted from the dental apparatus and utilized to detect a distinct autofluorescence associated with one or more tooth anomalies, e.g., dental plaque/caries. When the tooth anomaly is detected, the dental apparatus may then be utilized to remove the tooth anomaly. Alternatively, the second higher light level may provide part or all of a gingivitis, halitosis, or tooth staining treatment.

Figures 1A, 1B:
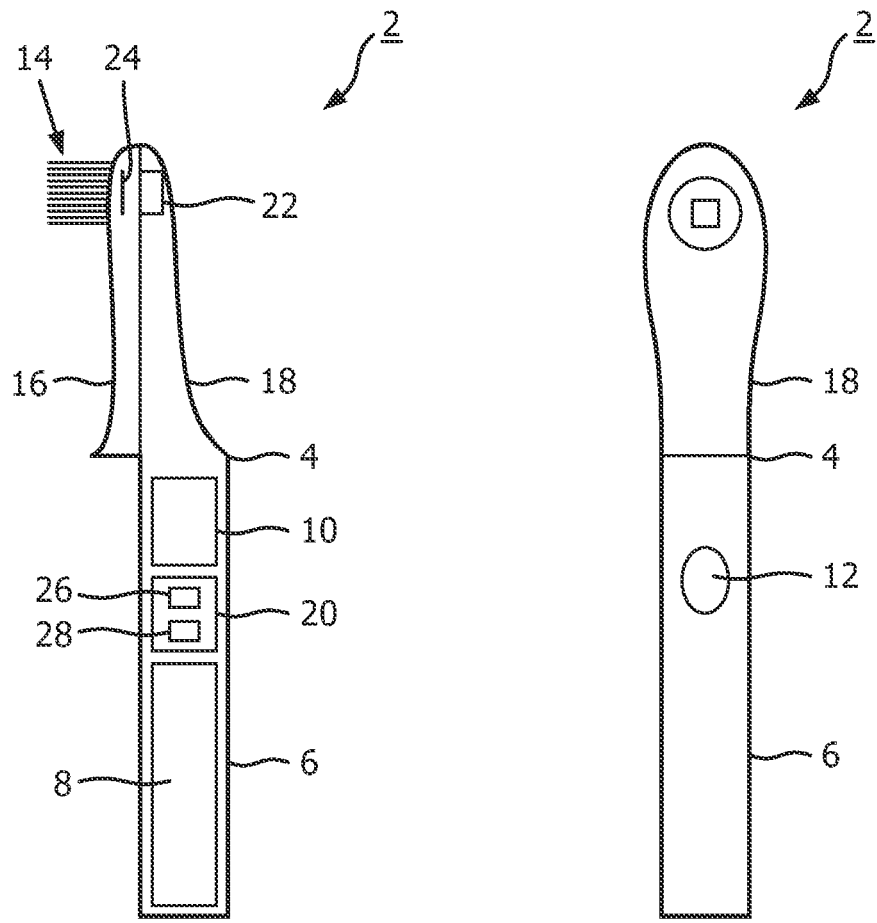
FIGS. 1A and 1B are side and front views, respectively, of a dental apparatus according to an embodiment of the instant disclosure.

FIG. 1A illustrates a system 2 that is configured to detect plaque/caries. System 2 includes a multipurpose dental apparatus 4 (e.g., a combination electric toothbrush and plaque/caries detector). Dental apparatus 4 includes a handle 6 of suitable configuration that is configured to house a battery 8 and an electric motor 10. A power button or switch 12 (FIG. 1B) is provided on the handle 6 and operably couples to battery 8 for supplying power to dental apparatus 4 and components operably associated therewith, e.g., electric motor 10, a controller 20, etc., when depressed. A plurality of bristles 14 of suitable configuration is provided on toothbrush assembly 16 that is configured to detachably couple via one or more coupling methods, e.g., clips (not explicitly shown), to a shaft 18 that extends distally from handle 6.

Figure 2:
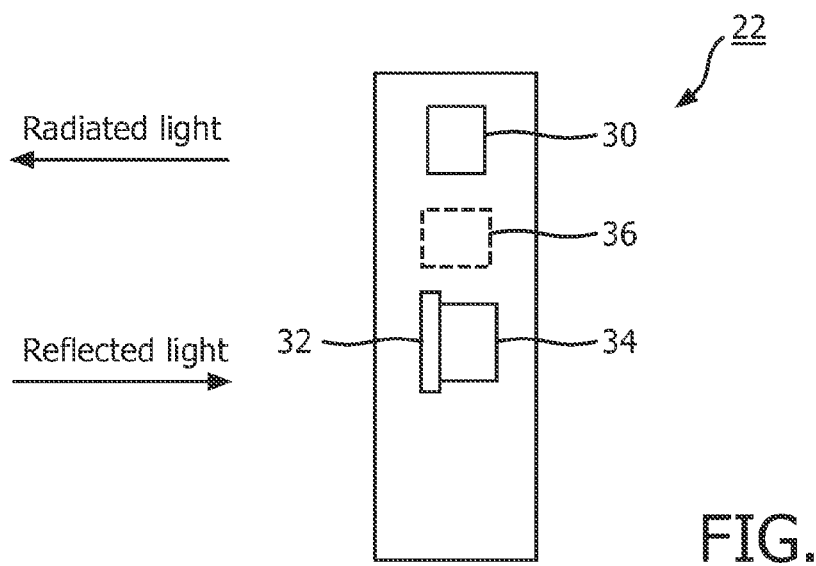
FIG. 2 is block diagram illustrating electrical circuitry of the dental apparatus.

FIG. 2 is block diagram illustrating electrical circuitry 22 of dental apparatus 4. Electrical circuitry 22 may include any suitable electrical components that are capable of generating, emitting and/or detecting various power intensities and frequencies of excitation light, e.g. blue light, red light etc. Electrical circuitry 22 may include, without limitation, for example, one or more light emitting diodes 30 (LEDs 30), filters 32, photodetectors 34 and/or imaging sensors 36 (imaging sensors 36 are shown in phantom in FIG. 2).

In the illustrated embodiment, a plurality of blue LEDs 30, one or more optical filters 32 and a plurality of photodetectors 34 were utilized to emit low and high intensities of excitation light and configured detect autofluorescence associated with tooth material and autofluorescence associated with one or more tooth anomalies, e.g., biofilms, dental plaque and caries (hereinafter collectively referred to as dental plaque). Alternatively, in embodiments, image sensors 36 may be utilized in place of photodetectors 34. In this particular embodiment, image processing may be utilized to convert pixel intensities into a form that can be used to determine when dental plaque has been detected. Specifically, image sensors 36 may be utilized to allow for dental plaque imaging so that only dental plaque present on a tooth triggers a signal. While photodetectors 34 and image sensors 36 are both suitable for detecting the aforementioned autofluorescence associated with tooth material and/or dental plaque, the simplicity of photodetectors 34 makes them ideal for the purposes described herein. As can be appreciated, dental apparatus 4 may include a combination of photodetectors 34 and imaging sensors 36. In order to shield photodetectors 34 and/or imaging sensors 36 from various frequencies of excitation light and/or unwanted background radiation, optical filters 32 may be mounted onto photodetectors 34 and/or imaging sensors 36.

Electrical circuitry 22 is configured to illuminate tooth material (and in some instances gums) from light emitted through toothbrush assembly 16 adjacent to where plurality of bristles 14 are disposed. With this purpose in mind, an optical window 24 (FIGS. 1A and 1B) of suitable of configuration is provided on toothbrush assembly 16 adjacent plurality of bristles 14 and is configured to allow light to pass therethrough for detection thereof by electrical circuitry 22. Specifically, when toothbrush assembly 16 is coupled to shaft 18, window 24 aligns with electrical circuitry 22 including LEDs 30, filters 32 and photodetectors 34 (and/or imaging sensors 36) such that light generated from LEDs 30 is emitted through window 24 and reflected light (e.g., autofluorescence of tooth material and/or dental plaque) is transmitted back through window 24 and detected by photodetectors 34 (or in some embodiments image sensors 36).

With reference again to FIG. 1A, dental apparatus 4 includes a controller 20 (e.g., a microprocessor) that communicates with electrical circuitry 22 (as best seen in FIG. 2) that is configured to generate, emit and detect light, e.g., low/high intensity excitation light and autofluorescence associated with tooth material and dental plaque. Controller 20 can be a processor, microcontroller, a system on chip (SOC), field programmable gate array (FPGA), etc. Collectively the one or more components, which can include a processor, microcontroller, SOC, and/or FPGA, for performing the various functions and operations described herein are part of a controller 20, as recited, for example, in the claims. Controller 20 can be provided as a single integrated circuit (IC) chip which can be mounted on a single printed circuit board (PCB). Alternatively, the various circuit components of controller 20, including, for example, the processor, microcontroller, etc. are provided as one or more integrated circuit chips. That is, the various circuit components may be located on one or more integrated circuit chips.

To this end, controller 20 includes a mouth detection module 26 and a tooth anomaly module 28. Controller 20, via mouth detection module 26 and tooth anomaly module 28, is configured to control operation of dental apparatus 4 in two modes of operation, a mouth detection mode and a tooth anomaly detection mode. In accordance with instant disclosure, these two modes of operation modes are configured to collectively protect the eyes of a user from potentially harmful and/or annoying light glare that may be attributed to the low and/or high intensity of excitation light and/or autofluorescence associated with tooth material and dental plaque.

Mouth detection module 26 and tooth anomaly module 28 communicate with each other and/or controller 20 and are configured such that when autofluorescence associated with tooth material is detected, a control signal from mouth detection module 26 is sent to controller 20 for placing dental apparatus 4 in the tooth anomaly detection mode for detecting autofluorescence associated with dental plaque. In the illustrated embodiment, controller 20 utilizes a closed loop feedback loop to continuously and automatically adjust power levels of the emitted wavelengths of excitation light to protect the eyes of a user. Thus, if autofluorescence of tooth material is not detected by mouth detection module 26, the high intensity excitation light is not generated and/or emitted from dental apparatus 4. In embodiments, such as the illustrated embodiment, controller 20 may be configured to default to mouth detection mode when dental apparatus 4 is initially powered.

Through empirical testing it has been found that blue light is, typically, 2-3 times more sensitive in magnitude than red light when utilized for detecting tooth material and/or dental plaque. In accordance with the instant disclosure, low intensity blue light is, initially, utilized to detect tooth material and high intensity blue light is utilized to detect dental plaque. As can be appreciated, the aforementioned drawbacks (e.g., eye glare and/or endangering the eyesight of the user) that are typically associated with dental apparatuses that utilize red light, e.g., infrared light, are reduced, if not, eliminated by utilizing low and/or high intensity blue light.

In mouth detection mode, low intensity blue light (e.g., having a power<1 mW at 405 nm wavelength), which has been found to be eye-safe, is emitted through window 24 for detecting tooth material. Specifically, when the low intensity blue light is emitted into the mouth of a user, autofluorescence of the tooth material is return through window 24 to photodetectors 34, which is set for a specific current threshold. Thus, if the detected autofluorescence of the tooth material is sufficiently strong, teeth are considered to be detected enabling the plaque detection mode to be enabled.

When controller 20 detects that dental apparatus 4 is inside the mouth, dental plaque detection mode is initiated enabling the low intensity excitation light to be increased to a high or full intensity excitation light (e.g., having a power>1 mW at 405 nm wavelength). It has been found that the high intensity excitation light should be approximately five times (5×) greater than the low intensity excitation light. As described above with respect to the low intensity excitation light and tooth material, dental plaque will also autofluoresce and be received by photodetectors 34. In the illustrated embodiment, the light detected as a result of the autofluorescence of dental plaque is passed through one of two filters 32 that are arranged at >425 nm; this is specific for blue (405 nm) light excitation. Filters 32 may be arranged in other configurations to accommodate different wavelengths and/or power intensities of blue light and/or to achieve different filtering outcomes.

In accordance with the instant disclosure, the low or high intensity excitation lights may be provided as a continuous light or a trail of pulses alternating between the low and high intensities of excitation light. Moreover, light created as a result of autofluorescence of tooth material and/or dental plaque may undergo a frequency shift that is caused by the autofluorescence which is detected by photodetectors 34 (or imaging sensors 36). Consequently, the non-frequency shifted light is blocked by filters 32 and not received by photodetectors 34 (or imaging sensors 36).

Operation of system 2 is described in terms of a method 100 for detecting dental plaque/caries. Dental apparatus 4 may, initially, be positioned within a mouth of a user (see FIG. 4 at step 102). When the dental apparatus 4 is powered on, plurality of bristles 14 are rotated, in conventional fashion, and a low intensity excitation light is emitted from LEDs 30 (see FIG. 4 at step 104) which causes tooth material to autofluoresce (see FIG. 4 at step 106). As noted above, the low intensity excitation light may be by a pulse of excitation light at a low power level. The wavelength shifted fluorescence signal is received by photodetectors 34 (or image sensors 36). Mouth detection module 26 receives a signal from photodetectors 34 and sends a corresponding signal to controller 20 indicating that dental apparatus 4 is positioned within a mouth of a user.

Figure 3:
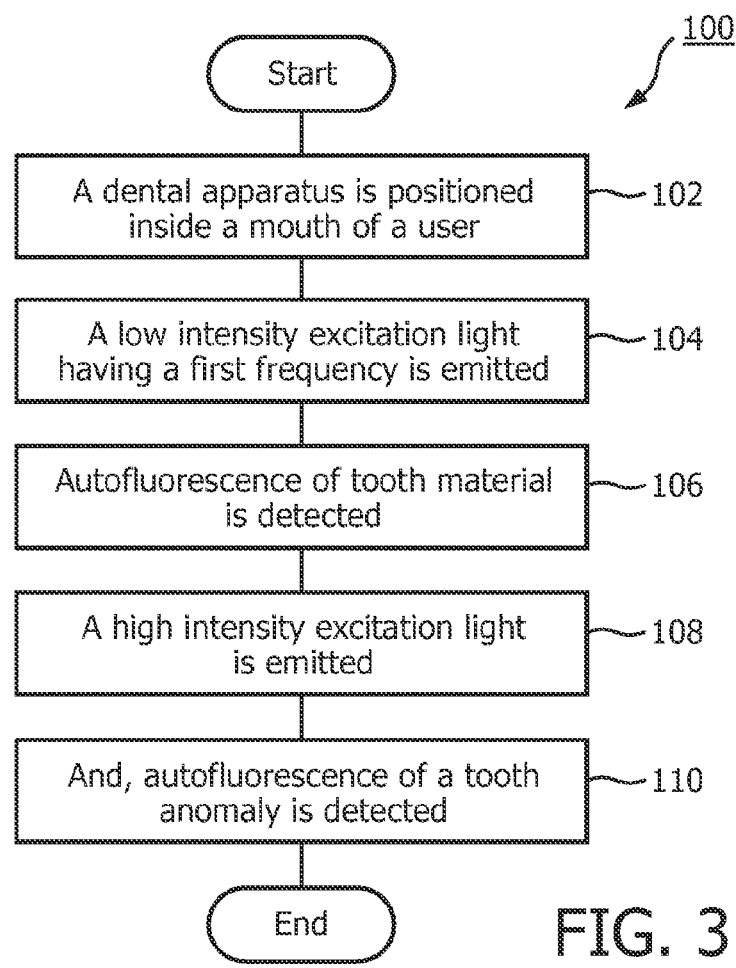
FIG. 3 is a flow chart illustrating a method of detecting plaque.

Thereafter, controller 20 sends a command signal to plaque detection module 28 and high intensity excitation light is then generated from LEDs 32 (see FIG. 4 at step 108) which causes dental plaque to autofluoresce (see FIG. 3 at step 110). In accordance with the instant disclosure, autofluorescence of tooth material is continuously monitored by controller 20 to ensure dental apparatus 4 remains in the mouth; this ensures that the high intensity excitation light is maintained within mouth.

The aforementioned process repeats to continuously measure a level of plaque on the current tooth being brushed. Dental apparatus 4 can communicate the presence of plaque to the user in a wide variety of ways e.g. by illuminating one more LEDS on handle 8 (not explicitly shown).

Dental apparatus 4 enables high intensity excitation light to be used inside the mouth to detect dental plaque while taking into considerations adequate eye safety protection that is essential for consumer safety. In addition, the likelihood of misuse by a user is reduced, if not eliminated, as a result of controller 20 utilizing a continuous monitoring feedback loop that provides "self testing" to ensure that dental apparatus 4 is positioned within a mouth of a user before enabling dental plaque detection mode, which utilizes high intensity excitation light. In addition, because dental apparatus 4 utilizes the same illumination source, e.g., a blue LED 30, manufacturing costs are minimized.

From the foregoing and with reference to the various figure drawings, those skilled in the art will appreciate that certain modifications can also be made to the present disclosure without departing from the scope of the same. For example, in some embodiments, electrical circuitry 22 may be built into handle 8 to allow shaft 18 to be replaced. In this instance, the low and high intensity excitation light may be delivered to toothbrush assembly 16 and reflected light returned to controller 20 including mouth detection module 26 and/or dental plaque detection module 28 via optical fibers (not explicitly shown). Moreover, in this embodiment, one or more light guides (not explicitly shown) may be provided on dental apparatus 4 and configured to channel light to and from window 24.

Moreover, time modulation of low and/or high intensity excitation lights can be used to allow background signals to be subtracted away; this may eliminate some of the potentially interfering background radiation present within the mouth.

Further, while it has been described herein to utilize high and low intensities of excitation light that is blue, it is within the purview of the instant disclosure to utilize high intensity excitation light having a different frequency. For example, red light, e.g., infrared light, may be utilized.

While the aforementioned dental apparatus 4 has been described herein as being utilized to detect one of more of the aforementioned tooth anomalies, it is within the purview of the instant disclosure to utilize dental apparatus 4 to detect one or more other dental conditions that may be present in the oral cavity. For example, dental apparatus 4 may be utilized as a gum shield. In this embodiment, dental apparatus 4 may be configured to detect when it is in the mouth utilizing the aforementioned low intensity excitation light and, subsequently, utilizes a high intensity excitation light having one or more of the aforementioned frequencies, e.g., blue light and/or red light, to detect the presence of and treat halitosis and/or gingivitis. Moreover, dental apparatus 4 may be configured for teeth whitening. In this instance, the high intensity excitation light may be utilized in connection with one or more tooth whitening regiments.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A dental apparatus, comprising:
a handle including a power button configured to place the dental apparatus in on/off configurations;
a controller housed within the handle and including a mouth detection module and a tooth anomaly module; and
electrical circuitry in operable communication with the mouth detection module and tooth anomaly module and configured to emit (i) a low intensity excitation light having a first frequency and a power less than 1 mW and (ii) a high intensity excitation light having a power greater than 1 mW but less than 5 mW;
wherein the controller is configured to, when the dental apparatus is in an on configuration, control the electrical circuitry to: (i) via the mouth detection module, utilize low intensity excitation light to detect the presence of tooth material; and (ii) via the tooth anomaly module, utilize the high intensity excitation light to either (a) detect the presence of a tooth anomaly or (b) treat a dental condition;

wherein the controller further is configured to, utilizing a closed loop feedback, continuously and automatically adjust power levels of emitted wavelengths between the high intensity and the low intensity levels of excitation light to protect a user's eyes from the high intensity excitation light, such that, if an autofluorescence of tooth material is not detected via the mouth detection module, then the high intensity excitation light is not generated or emitted via the electrical circuitry.

2. The dental apparatus according to claim 1, wherein the high intensity excitation light has a second frequency.

3. The dental apparatus according to claim 1, wherein the tooth anomaly is selected from the group consisting of biofilms, dental plaque and caries.

4. The dental apparatus according to claim 1, wherein a battery is housed within the handle and is configured to supply power to the dental apparatus including a motor that is housed within the handle and the electrical circuitry, which is housed in a shaft that extends distally from handle.

5. The dental apparatus according to claim 3, further including a toothbrush assembly that is configured to releasably couple to the shaft for at least brushing teeth and removing the tooth anomaly.

6. The dental apparatus according to claim 5, wherein a window is positioned on the toothbrush assembly adjacent a plurality of bristles provided thereon and aligns with the electrical circuitry disposed on the shaft such that the high and low intensity excitation light is emitted through the window and into a mouth of a user.

7. The dental apparatus according to claim 2, wherein a power of the high intensity excitation light is at least 5 times greater than a power of the low intensity excitation light and the first frequency is substantially equal to the second frequency.

8. The dental apparatus according to claim 1, wherein the electrical circuitry includes at least one of a light emitting diode, a filter, a photodetector and an imaging sensor.

9. The dental apparatus according to claim 1, wherein the dental apparatus is operable in two modes of operation, a mouth detection mode that is configured to detect the presence of the tooth material and a dental plaque detection mode that is configured to detect the presence of the tooth anomaly.

10. The dental apparatus according to claim 9, wherein the controller is further configured to automatically switch between the mouth detection mode and dental plaque detection mode and configured to automatically default to the mouth detection mode in response to (i) the dental apparatus being initially powered in an on configuration and (ii): the dental apparatus being removed from a mouth of a user.

11. The dental apparatus according to claim 10, wherein autofluorescence associated with the tooth material and the tooth anomaly is detectable by the electrical circuitry and communicated to the controller for placing the dental apparatus in the mouth detection mode and dental plaque detection mode, respectively.

12. The dental apparatus according to claim 11, wherein, in the dental plaque detection mode, the controller is configured to continuously detect autofluorescence associated with the tooth material while continuously detecting autofluorescence associated with the tooth anomaly.

13. The dental apparatus according to claim 1, wherein the dental condition is selected from the group consisting of tooth stains, gingivitis and halitosis.

14. The dental apparatus according to claim 4 wherein the dental condition is selected from the group consisting of tooth stains, gingivitis and halitosis.

15. A method to detect the presence of a tooth anomaly or treat a dental condition, the method comprising the steps of:

providing a dental apparatus comprising: (i) a controller comprising a mouth detection module and a tooth anomaly module; and (ii) electrical circuitry in operable communication with the mouth detection module and tooth anomaly module and configured to emit a low intensity excitation light having a first frequency and a power less than 1 mW, and a high intensity excitation light having a power greater than 1 mW but less than 5 mW;

detecting, via the mouth detection module, a presence of tooth material using the low intensity excitation light;

emitting, only if the presence of tooth material is detected by the mouth detection module, the high intensity excitation light; and utilizing, via the tooth anomaly module, the emitted high intensity excitation light to either (a) detect the presence of a tooth anomaly or (b) treat a dental condition;

wherein the controller, utilizing a closed loop feedback, continuously and automatically adjusts power levels of emitted wavelengths between the high intensity and the low intensity levels of excitation light to protect a user's eyes from the high intensity excitation light, such that, if an autofluorescence of tooth material is not detected via the mouth detection module, then the high intensity excitation light is not generated or emitted via the electrical circuitry.

* * * * *